United States Patent [19]

Yoshikawa et al.

[11] Patent Number: 4,594,457
[45] Date of Patent: Jun. 10, 1986

[54] PROCESS FOR PRODUCING AQUEOUS FORMALDEHYDE SOLUTION

[75] Inventors: Kyugo Yoshikawa, Shirone; Tadahiro Matsuzawa, Yokohama, both of Japan

[73] Assignee: Mitsubishi Gas Chemical Company, Inc., Tokyo, Japan

[21] Appl. No.: 721,814

[22] Filed: Apr. 10, 1985

[30] Foreign Application Priority Data

Apr. 12, 1984 [JP] Japan .................................. 59-73759

[51] Int. Cl.[4] ............................................ C07C 47/052
[52] U.S. Cl. ...................................... 568/473; 568/472
[58] Field of Search ................................ 568/473, 472

[56] References Cited

U.S. PATENT DOCUMENTS

| 3,994,977 | 11/1976 | Aicher et al. | 568/473 |
| 4,119,673 | 10/1978 | Aicher et al. | 568/473 |
| 4,383,123 | 5/1983 | Ferris et al. | 568/473 |
| 4,454,354 | 6/1984 | Ferris et al. | 568/473 |

FOREIGN PATENT DOCUMENTS

| 0767014 | 11/1971 | Belgium | 568/473 |
| 0100809 | 2/1984 | European Pat. Off. | 568/473 |

Primary Examiner—Werren B. Lone
Attorney, Agent, or Firm—Armstrong, Nikaido, Marmelstein & Kubovcik

[57] ABSTRACT

An aqueous formaldehyde solution having a formaldehyde concentration of 37 to 60% by weight is produced with less consumption of methanol under methanol-rich mild reaction conditions from a feed gas containing methanol, air, and steam, and, if necessary, an inert gas by subjecting the feed gas to catalytic reaction over a silver catalyst, contacting the resulting product gas with absorbing water, thereby absorbing the formaldehyde into the absorbing water from the product gas in an absorption column, and recovering the desired aqueous formaldehyde solution as bottoms of the absorption column, wherein a total of a corresponding amount of water to that of steam to be added to the feed gas and a necessary amount of water for adjusting the concentration of the product aqueous formaldehyde solution is added to the top of the absorption column as the absorbing water, and an aqueous solution containing 0.1 to 3.0% by weight of methanol and 0.1 to 1.0% by weight of formaldehyde is withdrawn at an upper level of the absorption column as a side cut in a corresponding amount to that of the steam to be added to the feed gas and added to the feed gas before the reaction.

8 Claims, 2 Drawing Figures

PROCESS FOR PRODUCING AQUEOUS FORMALDEHYDE SOLUTION

BACKGROUND OF THE INVENTION

This invention relates to a process for producing an aqueous formaldehyde solution having a particularly low methanol content by catalytic reaction of a feed gas containing methanol, air and water over a silver catalyst.

According to the conventional process for producing formaldehyde by oxidative dehydrogenation of methanol, a feed gas containing raw material methanol, air and steam, and further containing, if necessary, a waste gas, etc. is subjected to reaction over a silver catalyst, while recovering the heat of reaction from the resulting product gas in a boiler, if necessary, and the product gas is led to an absorption column to recover formaldehyde in the form of an aqueous solution. In that case, the methanol in excess over the air is used, and thus the resulting formaldehyde is usually contaminated with the unreacted remaining methanol. The remaining methanol itself has a stabilization effect on the formaldehyde solution, but the mere presence of methanol in excess is useless, and thus it has been now keenly desired to produce an aqueous formaldehyde solution having a low methanol content.

To this end, it is the ordinary expedient to increase a molar ratio of air to methanol to about 1.8, thereby decreasing the amount of remaining methanol in the product gas and obtaining formaldehyde having a low methanol content. In that case, steam is usually added to the feed gas to evade falling in the explosion range and control the reaction temperature. However, the steam remains in the product gas and condenses in the absorption column, thereby lowering the concentration of product aqueous formaldehyde solution. The concentration of the aqueous formaldehyde solution thus obtained is about 45% by weight at highest.

On the other hand, the so called waste gas recycle process, in which a portion of the waste gas from the absorption column is added to the feed together with steam, has been proposed as an effective means for lowering the methanol content of the product aqueous formaldehyde solution and enhancing the concentration of formaldehyde. Even in that process, the practical formaldehyde concentration of the product aqueous formaldehyde solution is about 55% by weight at highest.

When a molar ratio of air to methanol in the feed gas is increased, combustion reaction of methanol, and other side reactions proceed, and the selectivity to formaldehyde is liable to be lowered. Thus, it is preferable to make the molar ratio of air to methanol as low as possible.

SUMMARY OF THE INVENTION

An object of the present invention is to provide a process for producing an aqueous formaldehyde solution having a low methanol content and a high formaldehyde concentration, free from the said disadvantages, by conducting the reaction in milder conditions than those of the conventional process, while using a molar ratio of air to methanol in the feed gas of about 1.5 to about 1.6 when only steam is added to the feed gas, or using that of about 1.6 to about 1.8 when a waste gas is further added to the feed gas.

The present invention provides a process for producing an aqueous formaldehyde solution having a formaldehyde concentration of 37 to 60% by weight, which comprises subjecting a feed gas containing methanol, air and steam to catalytic reaction over a silver catalyst, contacting the resulting product gas with absorbing water, thereby absorbing the formaldehyde into the absorbing water from the product gas in an absorption column, and recovering the desired aqueous formaldehyde solution as bottoms of the absorption column, wherein a total of a corresponding amount of water to that of steam to be added to the feed gas and a necessary amount of water for adjusting the concentration of the product aqueous formaldehyde solution is added to the top of the absorption column as the absorbing water, and an aqueous solution containing 0.1 to 3.0% by weight of methanol and 0.1 to 1.0% by weight of formaldehyde is withdrawn at an upper level of the absorption column as a side cut in a corresponding amount to that of the steam to be added to the feed gas, and added to the feed gas before the reaction.

The feed gas for use in the present invention contains methanol, air and steam, and, if necessary, can contain a gas inert to the reaction such as a waste gas after recovering formaldehyde from the reaction product gas. The feed gas containing no such inert gas as a waste gas contains 1.5 to 2.0 moles, preferably 1.6 to 1.8 moles of air and 0.2 to 0.8 moles, preferably 0.4 to 0.6 moles of steam per mole of methanol. The feed gas containing the inert gas contains 1.6 to 2.2 moles, preferably 1.8 to 2.0 moles of air, 0.2 to 0.6 moles, preferably 0.2 to 0.5 moles of steam, and 0.2 to 2.0 moles, preferably 0.4 to 1.5 moles of inert gas per mole of methanol.

The feed gas having the said composition is subjected to reaction over the conventional catalyst for producing formaldehyde such as electrolytic silver, etc. at a temperature of 580° to 680° C., preferably 620° to 650° C. and at a linear velocity of feed gas of 0.8 to 2.0 m/sec., preferably 1.0 to 1.5 m/sec., as calculated in terms of the standard condition. The resulting reaction product gas is a hot gas containing 11 to 25% by mole of formaldehyde and 0.2 to 2.0% by mole of methanol at a temperature of 580° to 680° C., and thus the reaction product gas is usually passed through a shell-and-tube type boiler provided right under the reactor, and cooled to a temperature of 120° to 160° C., and then led to an absorption column.

The absorption column is divided into these sections, i.e., upper section, intermediate section, and lower section. The upper section is in a tray column structure, whereas the intermediate and lower sections are in a packed column structure. Water is fed to the column top to absorb the formaldehyde from the reaction product gas introduced into the column at the column bottom. In the intermediate and lower packed column sections of the absorption column, the absorbing water, which is an aqueous formaldehyde solution, is withdrawn to the outside of the column at each bottom of the packed column sections as side cuts, and the withdrawn side cuts are cooled and then recycled to the corresponding respective tops of the packed column sections. The lower packed column section is kept at a temperature of 60° to 80° C., and the intermediate packed column section is kept at a temperature of 20° to 30° C. by such outside cooling. As a result, in the lower packed column section, most of formaldehyde and a portion of methanol can be absorbed and condensed, whereas in the intermediate packed column section, a substantially whole amount of formaldehyde and a half amount of methanol can be absorbed.

At the top of the upper tray column section as the highest section of the absorption column, a necessary amount of water for adjusting the concentration of an aqueous formaldehyde solution to be withdrawn as a product at the bottom of the absorption column is usually added to the column as absorbing water. However, an overhead gas discharged at the top of the absorption column as a waste gas still contains 600 to 2,000 ppm by mole of formaldehyde, 1,500 to 5,000 ppm by mole of methanol, 700 to 3,000 ppm by mole of methyl formate, etc. as a loss.

In the present invention, a necessary amount of water for adjusting the concentration of the product aqueous formaldehyde solution and a corresponding amount of water to that to be added to the feed gas are introduced into the absorption column at the top of the tray column section, while a corresponding amount of the absorbing water to the amount of water to be added to the feed gas is withdrawn to the outside of the column as a side cut at an intermediate level (corresponding to a level of 5th to 20th tray from the top of the upper tray column section having 10 to 25 trays in total) at which the absorbing water contains 0.1 to 3.0% by weight of methanol and 0.1 to 1.0% by weight of formaldehyde, and the thus withdrawn side cut is added to the feed gas and subjected to the reaction. Accordingly, the amount of water to be introduced at the top of the absorption column is twice to five times as large as that introduced according to the conventional process, and thus the contents of formaldehyde, methanol, methyl formate, etc. in the waste gas discharged at the top of the absorption column are considerably lowered. Furthermore, the side cut withdrawn at the intermediate level of the upper tray column section contains methanol in a weight 1 to 4 times, particularly 2 to 3 times as large as formaldehyde. The addition of such a side cut to the feed gas can decrease the methanol consumption per unit formaldehyde production, and also the withdrawal of unreacted methanol as the side cut can decrease the contamination of the product aqueous formaldehyde solution by methanol. That is, an aqueous formaldehyde solution having a low methanol content can be obtained in spite of the reaction under the methanol-rich reaction conditions.

The product aqueous formaldehyde solution obtained according to the present invention contains 37 to 60% by weight, preferably 45 to 60% by weight, of formaldehyde, and 0.5 to 3.0% by weight, preferably 0.5 to 1.0% by weight, of methanol, where the content of by-product formic acid is less than 100 ppm by weight, usually 50 to 60 ppm by weight. The absorbing water withdrawn as the side cut is heated at 60° to 80° C. by a heat exchanger, and vaporized through contact with feed air to form the feed gas.

According to the present invention, a larger amount of absorbing water is introduced into the absorption column at the top of the column than that introduced according to the conventional process, and as the result, not only the contents of unabsorbed components in the waste gas and the methanol consumption per unit formaldehyde production can be reduced, but also the reaction can be carried out under methanol-rich, mild reaction conditions on the basis of the recovery of unreacted methanol. This also leads to such an advantage as reduction in the amount of steam to be added to the feed gas. Thus, the present invention has very remarkable effects.

PREFERRED EMBODIMENTS OF THE INVENTION

Example 1

Figure 1:
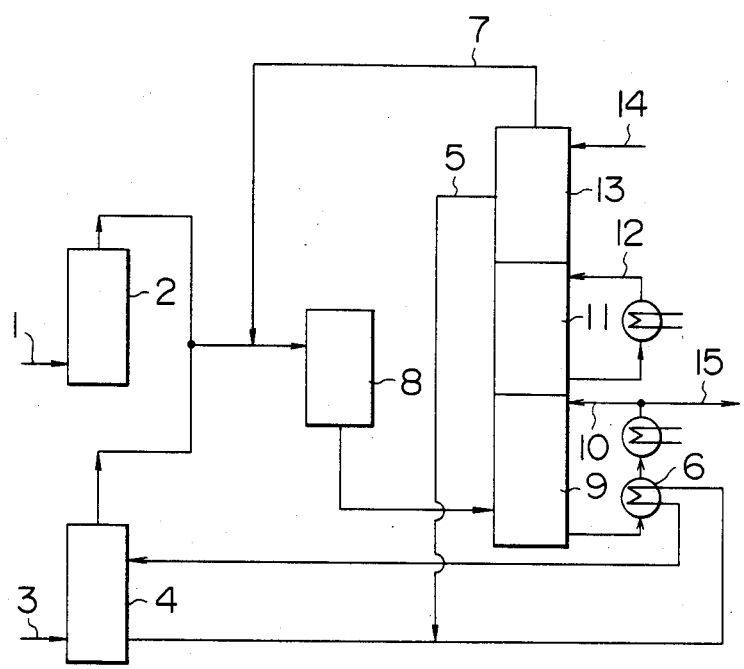
FIGS. 1 and 2 are flow diagrams of embodiments according to the present invention, respectively.

In FIG. 1, 2,410 kg/hr of methanol is led to vaporizer 2 through line 1 and vaporized, while 3,050 Nm$^3$ of air is led to humidifier 4 through line 3. 600 Kg/hr of side cut absorbing water is withdrawn from absorption column through line 5, heated to 65° C. in heat exchanger 6 and is led to humidifier 4. The side cut absorbing water contains 2% by weight of methanol. The air is contacted countercurrentwise in the humidifier 4 with 80 m$^3$/hr of the water at a temperature of 65° C. which is withdrawn from the bottom of the humidifier 4 and recycled to its top together with side cut water. The air leaving the humidifier has a temperature of 63° C., and the moisture content of the air leaving the humidifier 4 is adjusted by keeping the air at a constant temperature of 63° C. The heated methanol vapor and air are mixed, and the resulting feed gas mixture is led to reactor 8 together with waste gas discharged from the absorption column through line 7. The gas feed mixture at the inlet to the reactor has a molar ratio of methanol:air:steam:- waste gas of 1:1.8:0.4:1.3. In the reactor provided with a silver catalyst, formaldehyde is formed from the feed gas mixture by reaction at a reaction temperature of 620° C. The resulting reaction product gas is heat-exchanged with pressurized water in a waste heat boiler connected to the bottom of the reactor and cooled to 120° C. Then, the reaction product gas is led to the bottom of lower packed column section 9 of the absorption column, and countercurrentwise contacted with 140 m$^3$/hr of circulating water 10 (which is an aqueous formaldehyde solution) at 60° C., whereby most of formaldehyde and a portion of methanol are absorbed into the circulating water. The remaining reaction product gas is further countercurrentwise contacted with 140 m$^3$/hr of circulating water 12 (which is an aqueous formaldehyde solution) at 30° C. in intermediate packed column section 11 of the absorption column, whereby substantially all amount of formaldehyde is absorbed into the circulating water. Then, the unabsorbed reaction product gas is led to upper tray column section 13 of the absorption column, and countercurrentwise contracted with 700 kg/hr of absorbing water at 20° C. introduced at the column top through line 14, whereby methanol and formaldehyde are substantially completely absorbed into the absorbing water. The waste gas discharged at the column top contains only 100 ppm by mole of formaldehyde, 300 ppm by mole of methanol and 400 ppm by mole of methyl formate. The product aqueous formaldehyde solution containing 55% by weight of formaldehyde, 1.0% by weight of methanol and 50 ppm by weight of formic acid was obtained through line 15 at a rate of 3,650 kg/hr.

Example 2

Figure 2:
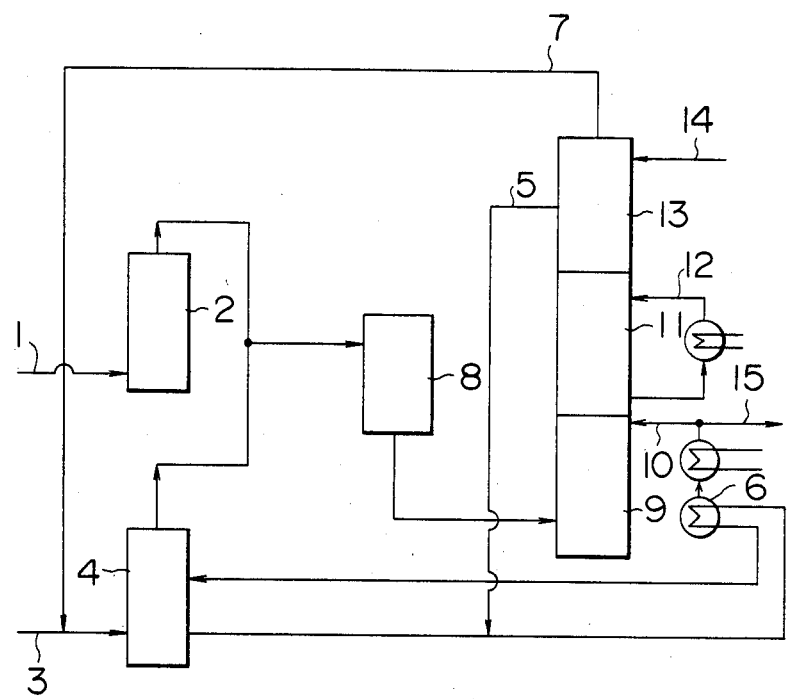

As shown in FIG. 2, the waste gas 7 is led to the humidifier 4 together with the air from line 3 to increase the moisture content. Methanol 1 is vaporized in vaporizer 2 and mixed with humidified air and waste gas from humidifier 4. The resulting feed gas mixture at the inlet to the reactor 8 has a molar ratio of methanol:air:steam:- waste gas of 1:1.8:0.6:1.3. The reactor temperature is kept at 610° C., whereas the operating conditions of the absorption column is substantially the same as in Example 1, except that the amount of absorbing water introduced at the absorption column top through the line 14 is 1,000 kg/hr, and the amount of side cut absorbing water 5 is 900 kg/hr. The resulting product aqueous formaldehyde solution contains 51% by weight of formaldehyde, 0.7% by weight of methanol, and 50 ppm by weight of formic acid, whereas the waste gas contains 80 ppm by mole of formaldehyde, 250 ppm by mole of methanol and 350 ppm by mole of methyl formate.

Example 3

In FIG. 1, 2,250 kg/hr of methanol is led to vaporizer 2 through line 1 and vaporized, while 2,530 Nm$^3$/hr of air is led to humidifier 4 through line 3. 900 Kg/hr of side cut absorbing water is withdrawn from absorption column through line 5, heated to 65° C. in heat exchanger 6 and is led to humidifier 4. The side cut absorbing water contains 1.7% by weight of methanol. The air is contacted countercurrentwise in the humidifier 4 with 80 m$^3$/hr of the water at a temperature of 65° C. which is withdrawn from the bottom of humidifier 4 and recycled to its top together with side cut water. The air leaving the humidifier has a temperature of 62° C., and the moisture content of the air leaving the humidifier 4 is adjusted by keepting the air at a constant temperature of 62° C. The heated methanol vapor and air are mixed, and the resulting feed gas mixture is led to reactor 8 without mixing with the waste gas discharged from the absorption column through line 7. The gas feed mixture at the inlet to the reactor has a molar ratio of methanol:air:steam of 1:1.6:0.7. In the reactor provided with a silver catalyst, formaldehyde is formed from the feed gas mixture by reaction at a reaction temperature of 620° C. The resulting reaction product gas is heat-exchanged with pressurized water in a waste heat boiler connected to the bottom of the reactor and cooled to 110° C. Then, the reaction product gas is led to the bottom of lower packed column section 9 of the absorption column, and countercurrentwise contacted with 140 m$^3$/hr of circulating water 10 (which is an aqueous formaldehyde solution) at 60° C., whereby most of formaldehyde and a portion of methanol are absorbed into the circulating water. The remaining reaction product gas is further countercurrentwise contacted with 140 m$^3$/hr of circulating water 12 (which is an aqueous formaldehyde solution) at 30° C. in intermediate packed column section 11 of the absorption column, whereby substantially all amount of formaldehyde is absorbed into the circulating water. Then, the unabsorbed reaction product gas is led to upper tray column section 13 of the absorption column, and countercurrentwise contacted with 1,400 kg/hr of absorbing water at 20° C. introduced at the column top through line 14, whereby methanol and formaldehyde are substantially completely absorbed into the absorbing water. The waste gas discharged at the column top contains 60 ppm by mole of formaldehyde, 200 ppm by mole of methanol and 300 ppm by mole of methyl formate. The product aqueous formaldehyde solution containing 47.6% by weight of formaldehyde, 3.4% by weight of methanol and 50 ppm of formic acid was obtained through line 15 at a rate of 3,890 kg/hr.

What is claimed is:

1. A process for producing an aqueous formaldehyde solution having a formaldehyde concentration of 37 to 60% by weight which comprises subjecting a feed gas containing methanol and, per mole of said methanol, 1.5 to 2.0 moles of air and 0.2 to 0.8 moles of an aqueous solution containing 0.1 to 3.0% by weight of methanol and 0.1 to 1.0% by weight of formaldehyde, said aqueous solution being obtained as a side cut from an absorption column used in the process, to catalytic reaction over a silver catalyst at a temperature of 580° C. to 680° C. to form a product gas; contacting the product gas with absorbing water in said absorption column to absorb the formaldehyde into the absorbing water from the product gas; recovering the desired aqueous formaldehyde solution as bottoms of the absorption column; withdrawing said aqueous solution containing 0.1 to 3.0% by weight of methanol and 0.1 to 1.0% by weight of formaldehyde at an upper level of said absorption column as a side cut in an amount corresponding to the amount used in the feed gas; combining said aqueous solution with methanol and air to form said feed gas; and adding an amount of water to the top of said absorption column corresponding to the total of the amount of said aqueous solution withdrawn as the side cut and an amount of water necessary for adjusting the concentration of the product aqueous formaldehyde solution.

2. A process according to claim 1, wherein an inert gas is added to the feed gas.

3. A process according to claim 2, wherein the inert gas is a waste gas from the absorption column.

4. A process according to claim 3, wherein the feed gas contains 1.6 to 2.2 moles of the air, 0.2 to 0.6 moles of said aqueous solution, and 0.2 to 2.0 moles of the waste gas per mole of the methanol.

5. A process according to claim 1, wherein the reaction is carried out at a temperature of 580° to 680° C. and at a linear velocity of feed gas of 0.8 to 2.0 m/sec, as calculated in terms of the standard condition.

6. A process according to claim 1, wherein the absorption column consists of an upper tray column section, an intermediate packed column section and a lower packed column section, and the side cut is withdrawn at an intermediate level of the upper tray column section.

7. A process according to claim 3, wherein the waste gas is added to a mixture of vaporized methanol and humidified air.

8. A process according to claim 3, wherein the waste gas is led to the bottom of a humidifier together with air.

* * * * *